(12) United States Patent
Rigling

(10) Patent No.: US 6,997,313 B2
(45) Date of Patent: Feb. 14, 2006

(54) WASTE CONTAINER, PARTICULARLY BIOHAZARD BIN FOR COLLECTING MEDICAL WASTE

(76) Inventor: Joachim Rigling, Schelmenweg 15, 75382 Althengstett (DE)

( * ) Notice: Subject to any disclaimer, the term of this patent is extended or adjusted under 35 U.S.C. 154(b) by 167 days.

(21) Appl. No.: 10/783,876

(22) Filed: Feb. 20, 2004

(65) Prior Publication Data
US 2004/0163981 A1    Aug. 26, 2004

(30) Foreign Application Priority Data
Feb. 22, 2003   (DE) ............................. 103 07 773

(51) Int. Cl.
*B65D 83/10* (2006.01)
(52) U.S. Cl. ...................... 206/366; 206/370
(58) Field of Classification Search .............. 206/1.5, 206/366, 370, 807; 220/256.1, 254.1, 319; 215/273
See application file for complete search history.

(56) References Cited

U.S. PATENT DOCUMENTS

| | | | | |
|---|---|---|---|---|
| 5,507,408 A | * | 4/1996 | Mosior et al. | ........... 220/345.2 |
| 5,823,340 A | * | 10/1998 | Maihofer | .................... 206/370 |
| 5,829,588 A | * | 11/1998 | Bloomfield | ................. 206/366 |

FOREIGN PATENT DOCUMENTS

DE          295 14 796       12/1995

* cited by examiner

*Primary Examiner*—David T. Fidei
(74) *Attorney, Agent, or Firm*—Klaus J. Bach

(57) ABSTRACT

In a hazardous waste collection container, particularly for medical waste, comprising a top part with a discard opening and a discard opening lid for opening and closing the discard opening, the discard opening lid comprises a retaining element and a closure element which is releasably engaged within the retaining element and the discard opening includes side walls with a closure collar provided with engagement means, and the closure member includes an engagement structure which is engaged by the engagement means of the closure collar when the closure member is pushed out of the retaining element into the discard opening for irreversibly locking the closure member in the discard opening.

19 Claims, 6 Drawing Sheets

US 6,997,313 B2

WASTE CONTAINER, PARTICULARLY BIOHAZARD BIN FOR COLLECTING MEDICAL WASTE

BACKGROUND OF THE INVENTION

The invention relates to a waste container, particularly a biohazard bin for collecting medical waste with a lower container part and a container top part which includes a discard opening and a lid and locking means for preventing access to the discard opening.

Such a biohazard bin is used for example for the disposal of one-way syringes, cotton swabs, scalpels and other medical waste. They include a lower container part and a container top part which is securely mounted onto the lower container part before the container is placed in use and which includes a waste discard opening with a closure lid.

DE 295 14 796 U1 discloses such a container with a circular opening in the top provided with an upstanding collar. A pot-like lid is connected to the collar by a retaining strip such that the opening can be closed when not in use, by pushing the pot-like lid into the collar to a first temporary closing position from which it is easily released for opening the container. If moved deeper into the collar to a second position, which is optically not well distinguishable from the first position the lid enters a locking position from which it cannot be removed, at least not without a special tool.

For a temporary and also for the final closing of the discard opening a lid may be provided on the top side of the container cover which, when closed, covers the discard opening but which is pivotable to an open position as shown for example in DE 198 47 619 C1. The lid may also be closed to two different engagement positions which are optically difficult to distinguish. In a first closed position, the lid extends over the upstanding collar of the discard opening from which position the lid can again be opened, but the lid can be pressed further onto the collar whereby it is locked to the collar such that it can no longer be removed.

It has been found that there is a need for a waste container which—with the repeatedly interrupted waste collection—has an easily operable temporary closure mechanism for a discard opening lid and a secure locking mechanism for the final closure of the discard opening. In addition, it should be possible to readily determine simply by viewing the container whether it is finally locked so that it should be passed on for disposition.

SUMMARY OF THE INVENTION

In a hazardous waste collection container, particularly for medical waste, comprising a top part with a discard opening and a discard opening lid for opening and closing the discard opening, the discard opening lid comprises a retaining element and a closure element which is releasably engaged within the retaining element and the discard opening includes side walls with a closure collar provided with engagement means, and the closure member includes an engagement structure which is engaged by the engagement means of the closure collar when the closure member is pushed out of the retaining element into the discard opening for irreversibly locking the closure member in the discard opening.

With the container according to the invention the following advantages are achieved:

For discarding waste, the lid is pivoted open whereby the discard opening becomes accessible. For temporarily closing the opening the lid is simply pivoted back to cover the opening, such that the discard opening lid consisting of the retaining element with the closure member covers the discard opening.

For the final, that is, irreversible closing of the discard opening the closure member is pressed for example with the thumbs of both hands downwardly out of the retaining element into the discard opening. To this end, only a resistance force of the engagement structure must be overcome by which the locking member is retained in the retaining element. During this step, the retaining element is supported by a rim area of the discard opening on which it is disposed.

Upon pressing the closure element, the locking collar of the closure element which is adapted to the inner width of the discard opening, moves successively out of the retaining element and into the discard opening. During the movement, the closure element comes into contact with the locking structure formed, depending on the design, in or around, the rim of the discard opening until it has assumed a position for final closure of the discard opening.

At this point, the locking structure of the locking collar becomes engaged with the locking structure of the rim or neck defining the discard opening, such that the closure member is firmly retained in the discard opening for permanently closing the container.

With the locking mechanism being inaccessible from the outside the final closure of the discard opening is very secure since then also the upper edge of the rim of the closure element may be disposed at the level of the edge of the discard opening or the surrounding upper side of the container top part so that there is no access to any structure that would permit the release of the locking structure.

When the closure member is pressed downwardly to its end position and is held in position on the seat by means of its locking collar, instead of a flat discard opening lid, only the retaining element which, earlier, provided a kind of a frame structure for the retaining element of the closure element is disposed in the edge area of the discard opening on the top of the container cover part. With this retaining element appearing "empty", it is readily apparent that the discard opening of the respective container is irreversibly closed and the container is ready for disposition.

Since the retaining element, which is now disposed "empty" on top side of the container cover, is still pivotable, it can be pivoted upwardly to serve as a handle for carrying the waste container. In this upwardly pivoted position, the final closure state of the container is furthermore signaled even more clearly.

It is advantageous if the discard opening is disposed in a flat depression on the top side of the container top part. The depth of the depression and the height of the support structure for the discard opening lid are adapted to each other. In this way, the discard opening lid can be received fully in the depression when the discard opening lid is closed, that is, it does not extend beyond the top side of the container top part. In this way, the lid is not only better protected from influences of the surrounding, but also the temporary closing of the discard opening by the lid which is supported at its edges is protected by the side walls of the container top part.

In addition, such a recess in the container top cover part improves the safety of the final closure member which is pressed into the discard opening or, respectively, its retaining member when seated. With such a recess, it is difficult to gain access from the side to the closure member when it is disposed lowered into the recess and locked therein in position by a locking structure which is also recessed and is therefore difficult to disable.

Preferably, the recess and, adapted thereto, also the discard opening and the discard opening lid have an elliptical shape. This shape results on one hand in a high stability of the closure member for the discard opening which is then also elliptical and, on the other hand, provides for an optimal discard opening which facilitates throwing waste into the container. This is particularly true if the main axis of the ellipse extends in a square container cover part for example up to two opposite side edges.

This advantage is not substantially negatively affected for example by a segment-like material bridge with a removal structure for injection needles, or respectively, needle holders, when compared with a circular discard opening of corresponding cross-section.

With regard to the about flat surface of the container cover part which permits the stacking of containers on top of one another when the discard opening is closed, the hinge structures supporting the discard opening lid are provided in a rectangular extension of the recess which receives the discard opening lid.

Preferably, the locking structure for the closure collar includes a number of spaced locking tongues disposed on the outside of the closure collar of the closure element which extend in an inclined fashion from the lower end area upwardly and project therefrom. With these elastic tongues, the locking element cannot only be held up to the final closure of the discard opening in the support element adapted thereto, which support element has a wall section which is adapted to the inclined locking tongues disposed between the upper and lower edges thereof and on which the locking tongues of the closure member arranged in the support element abut with a certain spring force.

Such tongues also facilitate pressing the closure member downwardly out of the support element whereby the tongues biased toward the locking collar such that the closure member can slide out of the support element.

Below the invention will be described in greater detail for a biohazard bin for collecting medical waste on the basis of the accompanying drawings.

DESCRIPTION OF A PREFERRED EMBODIMENT

Figure 1:
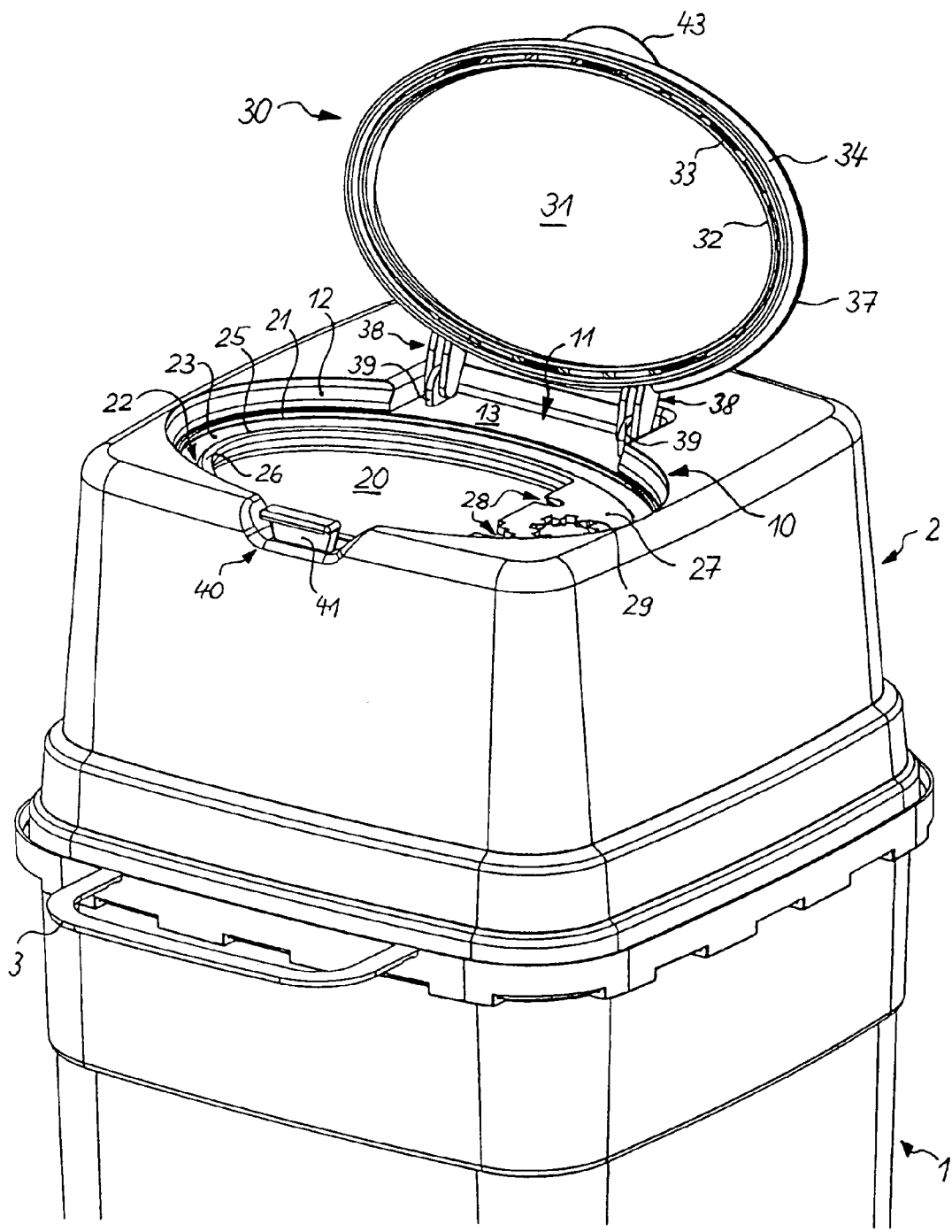
FIG. 1 is a perspective partial view of the waste container with the discard opening lid pivoted to its open position.

The waste container of which only the top is shown in the figures has a volumetric capacity of, for example, 5 or 7 liters. It includes a lower container part 1, which becomes narrower toward the bottom end thereof and a container top part 2, which becomes narrower toward the top end thereof. Both the lower and the top parts have an essentially square cross-section. They are firmly joined by a locking structure such that they sealed together and cannot be disconnected. To permit disposal of the container including its content by combustion, the container consists of a suitable plastic material.

The lower container part 1 is provided at opposite sides with handles 3 so that it can easily be carried during the time in which it is used for discarding hazardous waste.

On the top of the container top part 2, which has a top side edge length of for example 13 cm, a flat recess 10 is provided which, for an optimal size with regard to the square container top, has an elliptical shape. The recess 10 then extends over the full width of the container top part 2 and, in the front of the container, is disposed close to the front edge of the container. At the opposite side, the elliptical opening is extended rearwardly by a rectangular extension 11 beyond the center of the top part of the container. The side wall 12 of the recess 10 is inclined inwardly so that the cross-section of the recess 10 narrows downwardly.

At the base of the elliptical recess 10, an elliptical discard opening 20 is provided which has a cross-section that is, only slightly smaller than that of the recess 10. It forms a rim 21 with an essentially U-shaped seat structure 22 which extends around the opening 20 (see FIGS. 2, 6).

Figure 2:
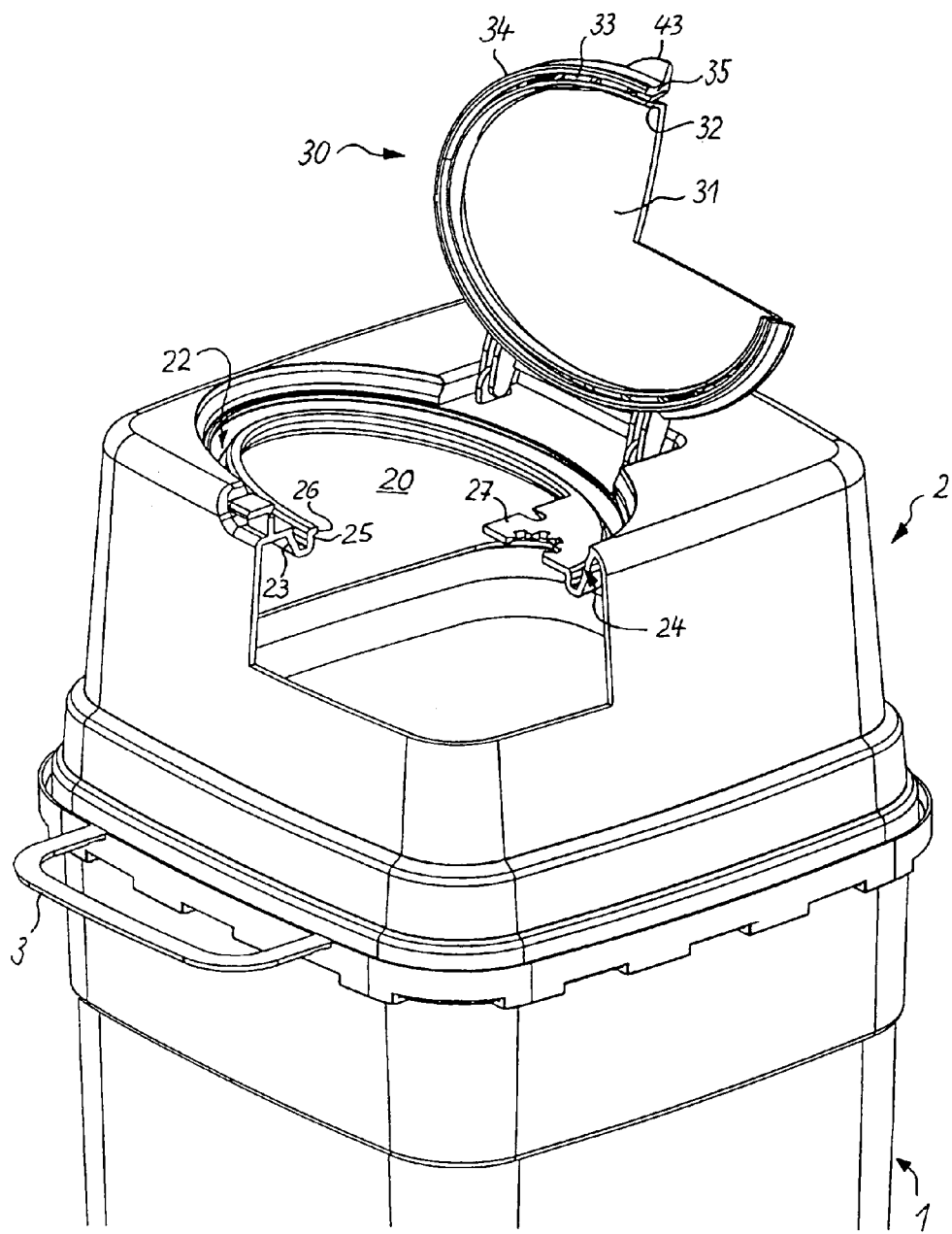
FIG. 2 is another perspective view of the container with portions cut away.
Figure 4:
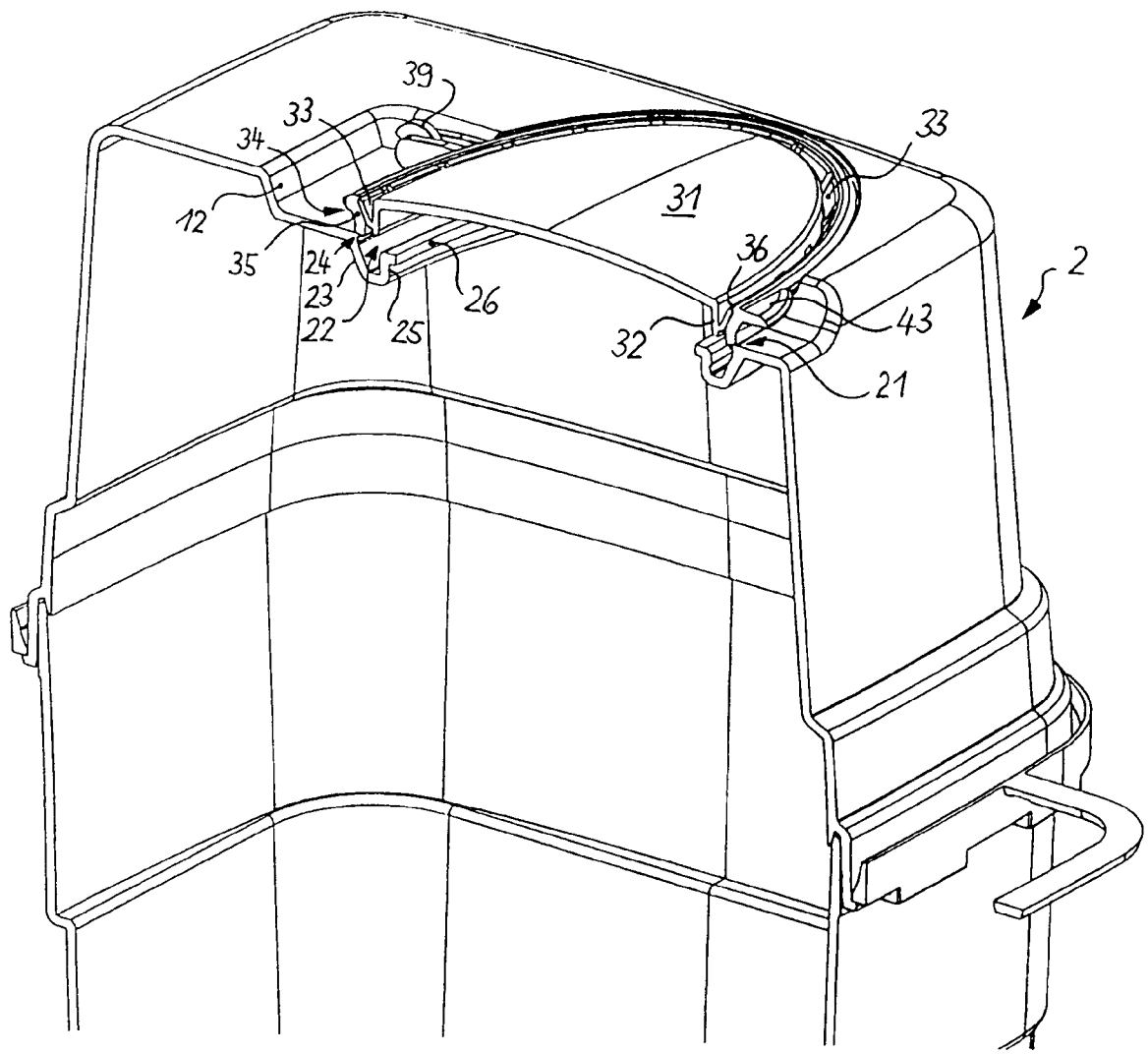
FIG. 4 is a cross-sectional view of the top part of the container.
Figure 6:
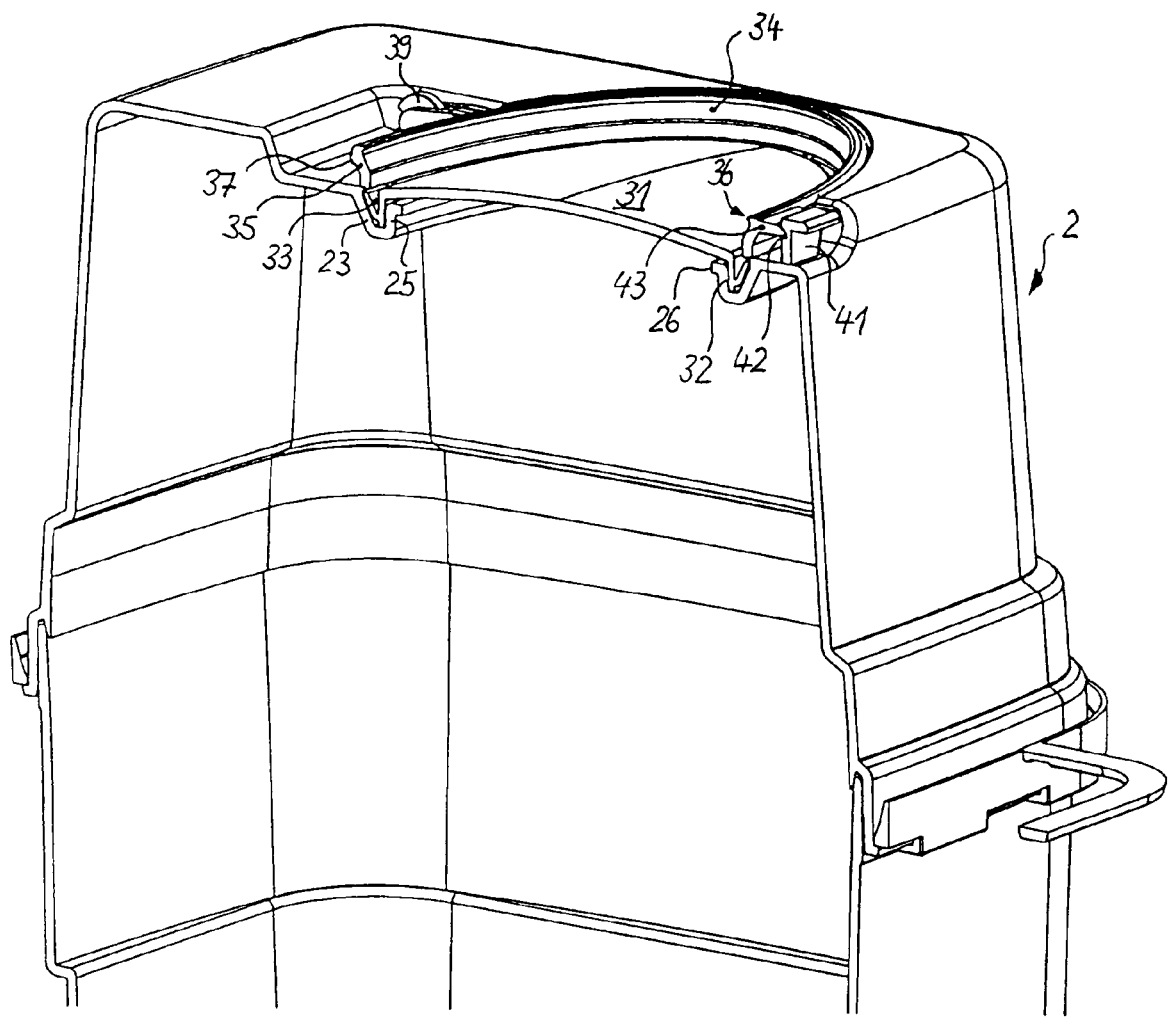
FIG. 6 is a cross-sectional view of the top part of the container with the closure member in the final closed position as shown in FIG. 5.

As shown more clearly in the sectional views of FIGS. 2, 4, 6, in the elliptical area of the recess 10, the outer leg 23 of the seat 22 is inclined in adaptation to the locking tongues 33 of the closing collar 32, which are also inclined so as to form conical engagement areas. The structure is formed as a downward extension of the inwardly inclined side wall 12 of the recess 10. The area of the rectangular extension 11 is formed by a corresponding deformation of the bottom wall 13 of the extension 11.

At the inside of the outer leg 23 of the U-shaped seat structure 22, an inwardly projecting locking lip 24 is provided on the upper rim which is disposed at the level of the bottom of the flat recess 10 or, respectively, the top surface of the bottom 13 of the rectangular extension 11. At this upper end of the shorter inner leg 25 of the U-shaped seat structure 22, an inwardly projecting reinforcement rib 26 is provided.

As shown in FIG. 1 at the right end of the discard opening 20, a bridge segment 27 extends across the discard opening 20. The bridge segment 27 includes cut-outs 28 and 29 shaped for drawing off injection needles and for unscrewing needle holders from syringe bodies.

For the temporary closing of the discard opening 20 (see FIGS. 3, 4), a discard opening lid 30 is provided which is adapted in its shape to the elliptical shape of the recess 30 or, respectively the rim 21 of the discard opening 20 and which consists of two parts. One part is a plate-like closure element 31, which is curved upwardly toward the center thereof for stabilization purposes for closing the discard opening 20. It is slightly smaller than the discard opening 20 and is provided with a closure collar 32 extending rectangularly downwardly from its circumferential edge. The inner diameter of the closure collar 32 and the outer diameter of the ring formed by the inner leg 25 of the seat 22 are adapted to each other.

At the outer circumference, the closure collar 32 is provided with spaced locking tongues 33 for locking the closure member 31 in a position in which the discard opening 20 is finally closed within the seat 22. The locking tongues 33 are arranged at a small distance from the lower edge of the closure collar 32 and extend upwardly close to the level of the upper outer edge of the closure member 31 at such an angle that they are elastically spaced from the closure collar 32 and engage the closure member 31.

The other part of the discard opening lid 30 is a retaining element 34, which has a height corresponding to the depth of the recess 10 and frame-like surrounds the closure element 31. It includes a circumferential wall section 35, which is inclined corresponding to the inclined tongues 33 of the closure member 31 so that its cross-section decreases from the upper to the lower end thereof that is its circumferential wall is inclined inwardly providing for an inwardly directed wall section 35.

At its upper edge, the retaining element 34 is provided at the inside thereof, with an inwardly projecting engagement lip 36 and at the outer circumference, it is provided with a circumferential reinforcement shoulder 37.

The discard opening lid 30 is formed by inserting the closure element 31 from above into the retaining element 34. During this step, the locking tongues 33 slide along the engagement lip 36 of the retaining element 34 and are pressed toward the closure collar 32 and then snap into an engagement position as shown in FIG. 4, in which they abut, under tension, the inlined wall section 35 of the retaining element 34. The edge of their free ends then abuts the underside of the engagement lip 36. In this way, the closure element 31 is prevented from being accidentally released from the retaining element 34 as it is engaged at its opposite sides in the retaining element 34.

The retaining element 34 is pivotally supported on the upper container part 2 by way of two support arms 38, which extend therefrom at one side. The support arms 38 are formed each by two spaced support webs which are pivotally mounted to support noses 39 extending upwardly from the bottom 13 of the extension 11 of the recess 10 up to the level of the top side of the container cover part 12. The support arms 38 are engaged by the support noses 39 such that the discard opening lid 30 is pivotable about an axis which is parallel to the top side of the upper container part 2.

Figure 3:
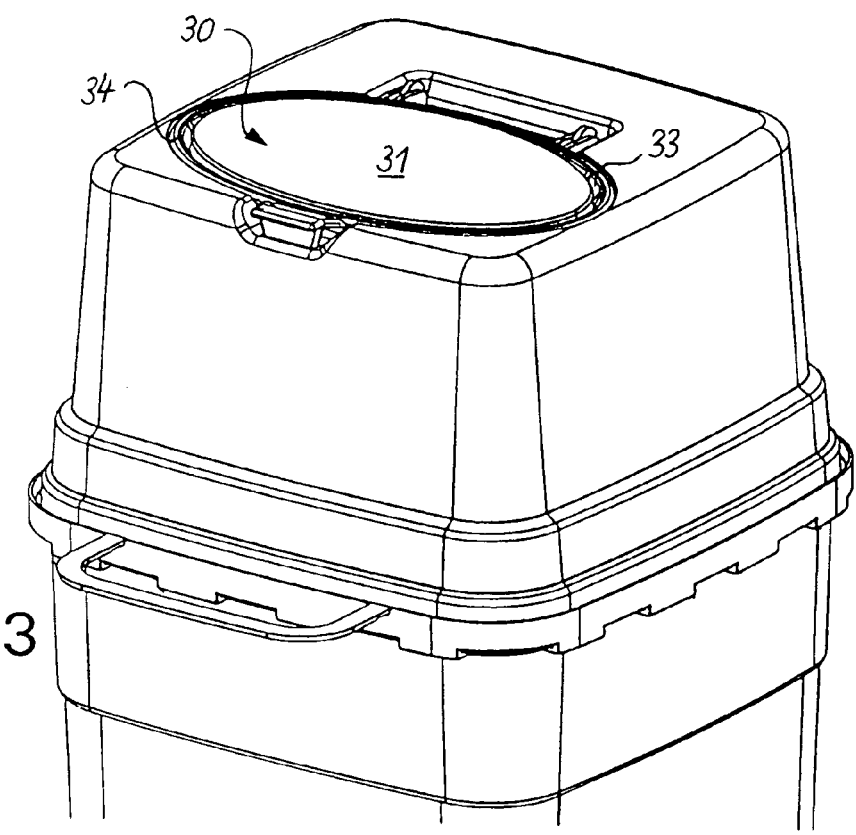
FIG. 3 shows the top part of the container with the discard opening lid closed for the temporary closure of the container.

For a temporary closure of the discard opening 20 by covering the opening 20 for example during a pause in the use of the container, the discard opening lid 30 is pivoted to its closed position, that is, it is pivoted from the position as shown in FIGS. 1 or 2, down into the position as shown in FIG. 3 or FIG. 4. It is then disposed in the recess 10 (FIG. 4), which is surrounded by the side wall 12 of the recess 10 and is protected thereby from damaging influences from without. The lid is then disposed with a narrow outer section of the lower edge of the retaining element 34 on the locking lip 24 which projects radially outwardly at the upper end of outer leg 23 of the U-shaped seat 22. In this position, the upper edge of the retaining element 34 extends essentially in the same plane as the upper edge of the elliptical recess 10 so that it does not project upwardly from the recess 10.

With the inwardly inclined side wall 12 of the recess 10, the discard opening lid 30 is centered when pivoted into the elliptical opening 20 by the wall section of the retaining element 34, whose circumferential outer wall is also inclined (FIGS. 3, 4).

For locking the discard opening lid 30 in this position in which it temporarily closes the discard opening, a locking recess 40 with an outwardly pivotable locking member 41 including a locking notch 42 at the inside thereof (FIG. 2, 6) is provided in the upper front edge of the container top part 2. When the discard opening lid 30 (FIG. 3) is pivoted down into the recess 10 a lock shackle 43 which extends outwardly from the retaining element 34 is engaged by the locking notch 42 to hold the discard opening lid 30 in its closed position. Other retaining structure however may be provided.

In this temporary closing position (FIGS. 3, 4), the discard opening lid 30 is disposed in the recess 10 and is surrounded by the side wall 12 such that it does not project upwardly from the top surface of the upper container part 2. It can therefore not easily be grasped for opening even when the lock shackle 43 is released from the locking member 41. So that it can still be easily pivoted to an open position a spring, for example a leg spring, may be provided at the pivot joint of at least one of the support arms 38 of the discard opening lid 30. This spring is tensioned when the lid 30 is closed. When the locking member 41 is pulled forwardly and the lock shackle 43 is released from the locking notch 42, the lid 30 moves automatically to its open position as shown in FIGS. 1 and 2, in which position it is held by the spring. Then, waste can be deposited in the container without the lid possibly closing by itself.

Such a spring-loaded opening mechanism for the discard opening lid 30 makes the use of the container not only more convenient but also safer: Because opening and closing of the lid 30 is simplified the persons using the waste container may open the lid with each use and close it thereafter so that the container remains closed most of the time.

For the final closing of the discard opening 20 (FIGS. 5, 6, 7), the closure element 31 is, with the lid 30 closed, that is, with the discard opening lid 30 in a locked position as shown in FIGS. 3 and 4, pushed down with the thumbs of both hands. At this point, the retaining element 34, which is centered in the recess 10 by the inclined side walls 12 of the recess 10 is supported at its lower edge by the locking lip 24. Upon forcing the closure member 31 downwardly, the locking tongues 33, by which the closure member 31 is held in the retaining element 34, are pressed toward the collar 32 and the closure member is released thereby from the retaining element 34 and is moved downwardly out of the retaining element 34.

Figure 5:
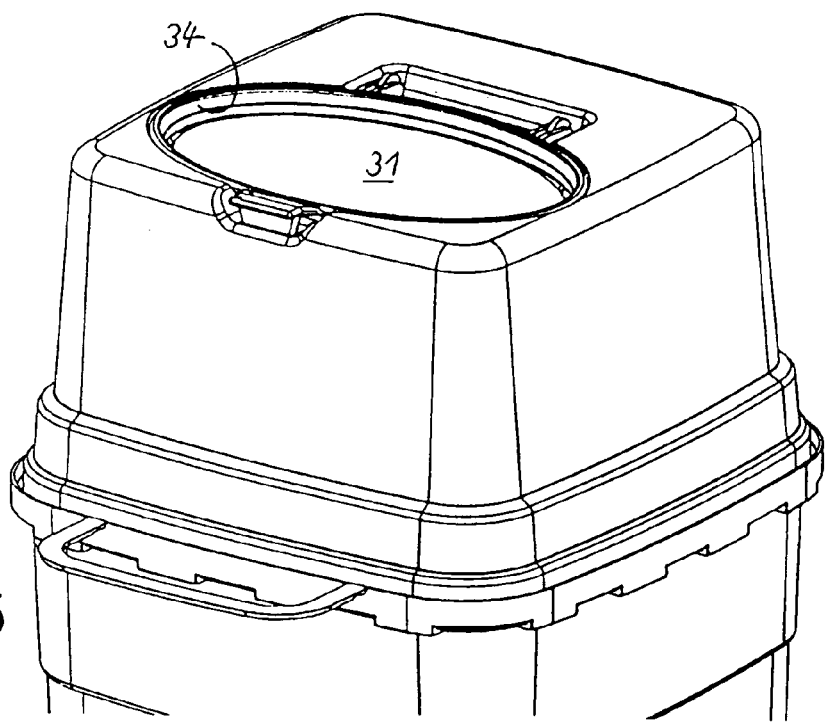
FIG. 5 shows the top part of the container with the discard opening finally closed by the discard opening lid.

Then successively, the closure collar 32 of the closure member 31 moves guided by the locking tongues 33 into the circumferential seat structure 22, which is in the form of a groove. Upon reaching its predetermined end position in the groove, the locking tongues 33 snap outwardly below the locking lip 24 at the edge of the outer leg 23 of the seat structure 22 and, in this way, hold the closure element 31 irreversibly in the seat structure 22 at the bottom of the recess 10 (FIGS. 5, 6).

To this end, the inner leg 25 of the seat structure 22 is somewhat shorter than the outer leg 23 in adaptation to the material thickness of the closure member 31. In the final locked position, the closure member 31 is disposed in the recess 10 with its upper edge at the level of the edge 21 of the discard opening so that it is well protected from manipulations. With the closure member 31 being level with the well bottom of the recess 10, it is also apparent that the container is permanently closed and can no longer be opened.

The base of the seat structure 22 may include a gasket cooperating with the lower edge of the closure collar 32 for tightly sealing the closure member 31 in the discard opening 20. A seal however may also be provided by the closure collar 32, which is spring-biased by the locking tongues 33 with the inner side thereof into engagement with the wall of the leg 25 of the seat structure 22.

With the position of the closure member 31 lowered in the discard opening, when it is in its final closing position at the bottom of the recess 10 as compared with a position level with the top wall of the upper container part 2, it is immediately indicated that the container is ready for disposition.

Figure 7:
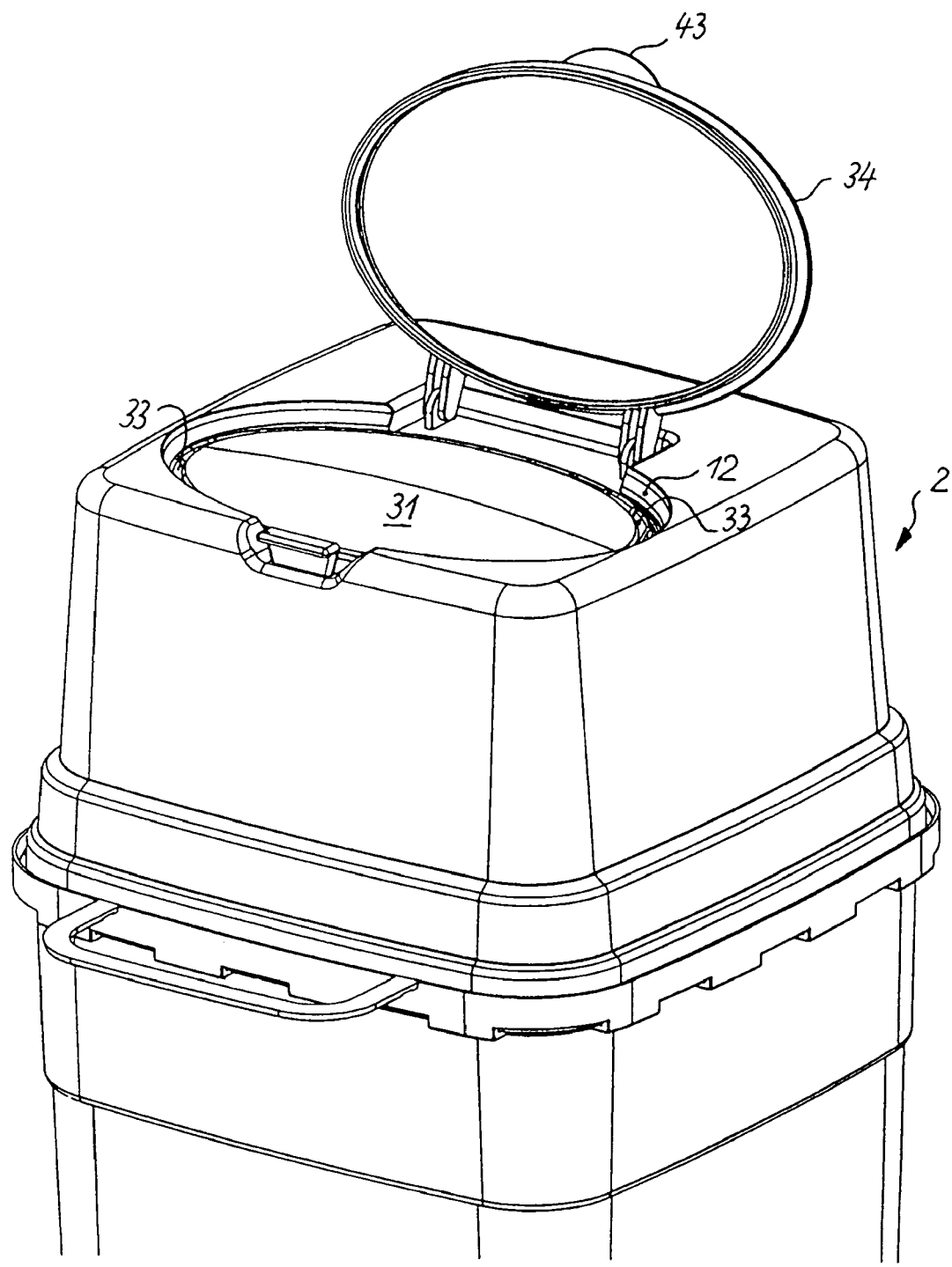
FIG. 7 shows the container top according to FIG. 5 with the closure member locked in the discard opening and the support element pivoted upwardly.

This situation can be accentuated or clearly signaled by pivoting the then empty retaining element upwardly to the position as shown in FIG. 7. This can simply be done by actuating the locking member 41 (FIG. 5), whereby the retaining element 34 is pivoted into an upright position by the release spring. If the retaining element 34 is sufficiently strong, it may even be used in this position for conveniently carrying a filled container.

With the concept of providing the discard opening lid 30 of a waste collection and disposition container in the form of a two-part member with a retaining element 34 and a closure member 31, which can be released from the retaining element 31 for the final closure of the waste container, a closure structure can be provided by which the discard opening 20 of the container can be temporarily closed and when filled can be irreversibly closed. When irreversibly closed, the closure member 31 is in a lowered position in the upper part of the container 2 and, by its position, indicates readily that the container is filled and ready for disposition. This situation can additionally signaled by pivoting the retaining element, which is then empty, into a noticeable upstanding position.

What is claimed is:

1. A hazardous waste collection container, particularly for medical waste, comprising: a lower container part (1), an upper container part (2) connected to said lower container part (1) and having a top end with a discard opening (20) formed therein, a discard opening lid (30) mounted on said upper container part (2) so as to be pivotable between an open position, in which access to said discard opening (20) is provided and a closed position, in which said discard opening lid (30) covers said discard opening (20), said discard opening lid (30) comprising a retaining element (34) and a closure member (31) releasably engaged within said retaining element (34), said discard opening (20) including side walls with a seat structure (22) and locking means (33) firmly engaging and irreversibly locking said closure member (31) in said discard opening (20) when said closure member (31) is pushed out of said retaining element (34) into said discard opening (20) below.

2. A container according to claim 1, wherein said seat structure (22) has a U-shaped circumferential configuration and is formed along the inner circumference of said discard opening (20) and said closure member (31) has a collar (32) which extends into said U-shaped seat structure (22) in said irreversibly locked position thereof.

3. A container according to claim 2, wherein said collar (32) provided with locking tongues (33) which are releasably engaged by said retaining element (34) for retaining said closure member (31) in said retaining element (34).

4. A container according to claim 3, wherein said seat structure (22) is provided with a locking lip (24) and said locking tongues (33) are engaged by said locking lip (24) in said discard opening when said closure element (31) is pushed out of said retaining element (34) into the irreversibly closed position in said discard opening (30).

5. A container according to claim 1, wherein said discard opening (20) is disposed in a flat recess (10) in the top of said upper container part (2), said recess (10) having a depth corresponding to the height of said retaining element (34).

6. A container according to claim 5, wherein said recess (10) and, in accordance therewith, said discard opening (20) have an elliptical shape.

7. A container according to claim 6, wherein said elliptical recess (10) is so arranged that, in the area of the smaller diameter of the elliptical recess (10), it is disposed close to a top edge of said upper container part (2).

8. A container according to claim 7, wherein, with a square upper container part (2), the area of the smaller diameter of the elliptical recess (10) is disposed adjacent a top front edge of said upper container part.

9. A container according to claim 8, wherein, in the area of the smaller diameter of the elliptical recess (10) opposite said front edge, said recess (10) includes a rectangular extension (11) having a bottom (13) from which two spaced support shackles (39) extend essentially up to the top of said upper container part for pivotally supporting said discard opening lid (30).

10. A container according to claim 5, wherein said recess (10) has side walls (12), which are inclined inwardly from the top of the upper container part (2) downward.

11. A container according to claim 4, wherein said locking tongues (33) are resilient and are disposed in circumferentially spaced relationship around said closure collar (32) and extend, outwardly inclined, upwardly from the lower end of said closure collar (32).

12. A container according to claim 11, wherein said retaining element (34) has downwardly inwardly inclined side walls so that its lower cross-section is smaller than the upper cross-section thereof in adaptation to the configuration presented by said locking tongues (33).

13. A container according to claim 12, wherein said retaining element (34) is provided at its upper edge with an engagement lip (36) projecting inwardly into said discard opening (30) for engaging said locking tongues (33) when said closure member (31) is disposed in said retaining element (34).

14. A container according to claim 1, wherein said seat structure (22) includes a seal for sealingly engaging said closure member (31) in its final locked position in said discard opening (30).

15. A container according to claim 9, wherein, in accordance with the distance between said spaced support shackles (39), two support arms (38) extend sidewardly from said retaining element (34), each support arm comprising spaced parallel webs joined at their free ends by a shaft and said shackles (39) have openings receiving said shaft for pivotally supporting said retaining element (34).

16. A container according to claim 5, wherein said upper container part (2) is provided with a locking member (41) for releasably holding said discard opening lid (30) in said recess (10) for covering said discard opening (20).

17. A container according to claim 16, wherein said locking member (41) is disposed in a locking recess (40) extending outwardly from said flat recess receiving said discard opening lid (30) and said locking member (41) includes at its inner side a locking notch (42) adapted to receive a lock shackle (43) projecting from said retaining element (34) for releasably locking said discard opening lid (30) covering said discard opening (20) in said recess (10).

18. A container according to claim 16, wherein said discard opening lid is spring-biased in the pivotal opening direction.

19. A container according to claim 1, wherein a bridge segment (27) extends across part of said discard opening (20) and is provided with means for engaging, and pulling out, injection needles from devices in which they are mounted.

* * * * *